(12) United States Patent
Li-Jones

(10) Patent No.: US 8,495,922 B1
(45) Date of Patent: Jul. 30, 2013

(54) SAMPLING SYSTEM FOR GROUND LEVEL AIRCRAFT ENGINE PARTICLE MATTER (PM) EMISSION MEASUREMENT

(75) Inventor: Xu Li-Jones, San Diego, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 97 days.

(21) Appl. No.: 13/176,122

(22) Filed: Jul. 5, 2011

Related U.S. Application Data

(60) Provisional application No. 61/362,167, filed on Jul. 7, 2010.

(51) Int. Cl.
*G01N 1/14* (2006.01)

(52) U.S. Cl.
USPC .................................................. 73/864.34

(58) Field of Classification Search
None
See application file for complete search history.

(56) References Cited

U.S. PATENT DOCUMENTS

| | | | | |
|---|---|---|---|---|
| 6,460,400 | B1* | 10/2002 | Ichikawa | 73/23.31 |
| 2006/0130599 | A1* | 6/2006 | Graze, Jr. | 73/864.73 |
| 2007/0157701 | A1* | 7/2007 | Black | 73/23.31 |

* cited by examiner

*Primary Examiner* — Robert R Raevis
(74) *Attorney, Agent, or Firm* — Charlene A. Haley; Christopher L. Blackburn

(57) ABSTRACT

A sampling system for ground level aircraft engine PM emission measurements has been developed.

20 Claims, 4 Drawing Sheets

SAMPLING SYSTEM FOR GROUND LEVEL AIRCRAFT ENGINE PARTICLE MATTER (PM) EMISSION MEASUREMENT

CROSS-REFERENCE TO RELATED APPLICATIONS

This is a non-provisional application claiming the benefit of provisional patent application Ser. No. 61/362,167 filed on Jul. 7, 2010, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to sampling systems for emissions measurements, and more specifically, sampling systems for aircraft engine particle matter (PM) emission measurements.

BACKGROUND OF THE INVENTION

There are many engineering challenges in the aircraft PM emission measurement field: it is difficult to dilute aircraft exhaust at the probe tip; the exhaust pressure at the engine exit varies tremendously from idle to maximum power, which makes it extremely difficult for any one sampling system to provide adequate dilution and deliver samples with stable pressure downstream; and due to the harsh testing environment, the sampling line is normally long (up to 140 ft) and no inline pump is allowed for PM measurement. A vacuum pump at the end of the sample line to aid in sample transfer would result in a sample at sub-ambient pressure which could lead to PM measurement instrument malfunctioning. To overcome these difficulties, PM emission testing normally demands a large effort in test setup which translates into a high cost.

The Aircraft Environmental Support Office (AESO) of the US Navy has previously used the EPA Method 5 for aircraft PM emission testing. This method used a large probe to capture exhaust samples for gravimetric analysis. This method is time consuming (high cost) and has a high detection limit that is not suitable for testing the low emission modern engines.

New methods have been developed within the aircraft PM emission measurement community in the last decade. To preserve the PM properties emitted from an aircraft engine, probe tip dilution is recommended (SAE-AIR 6037), which make it extremely difficult and costly to perform the PM emission measurement. Currently, it is not clear how much the PM properties will be affected when the sample is diluted downstream instead of at the probe tip.

For practical purposes, it is necessary to evaluate whether downstream dilution can be used to yield similar emission data as probe tip dilution. It is desirable to establish a sampling system that can function smoothly under any power condition and be able to deliver exhaust samples through a long sampling line at a pressure level within the operating limits of PM measurement instruments.

Figure 1:
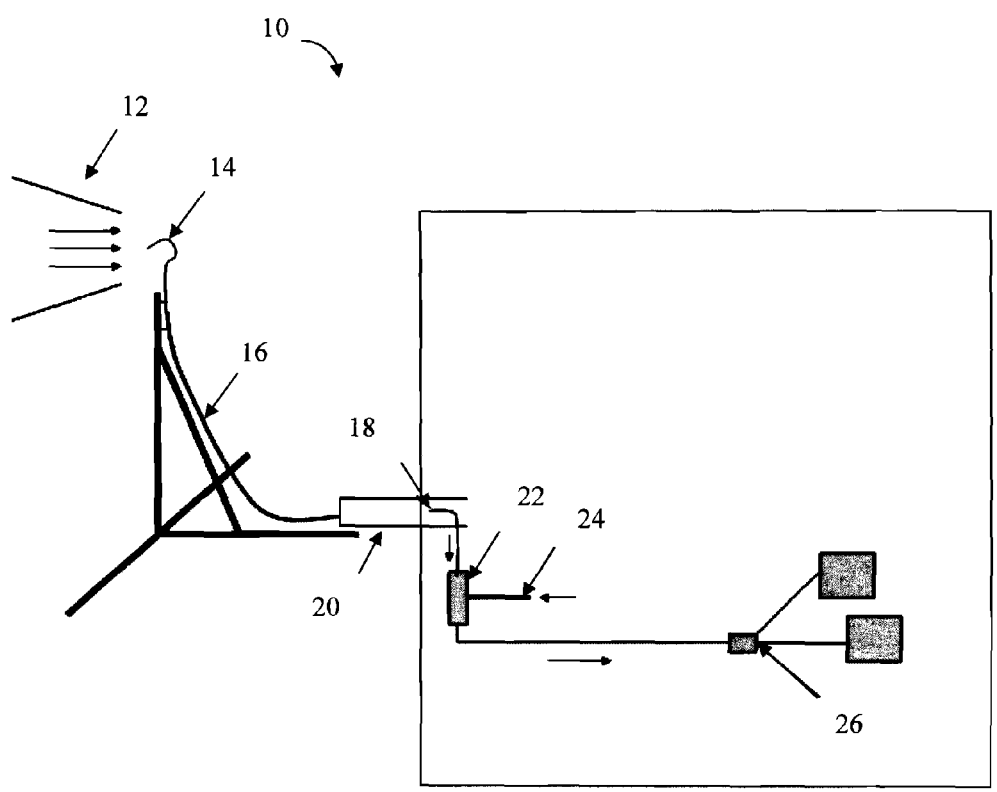
FIG. 1 is a sketch diagram showing an embodiment of a sampling system including three key components: a large inlet probe, an expansion chamber with one end open to the ambient atmosphere, and an ejector dilutor, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

The invention relates to sampling systems for ground level aircraft engine PM emission measurements.

Embodiments of the invention generally relate to sampling methods for testing particle emissions from aircraft engine(s) including, mounting one inlet probe at the aircraft engine exit plane with the probe inlet facing the exhaust plume substantially perpendicularly at the center of the plume 12 (shown in FIG. 1) cross section, associating one expansion chamber with the probe, where the probe is directing a flow of exhaust sample through the expansion chamber ensuring low particle matter resident time within the expansion chamber and allowing substantially no ambient air to enter the expansion chamber, expanding the exhaust sample within the expansion chamber with an inlet, discharging any excess exhaust through an open end to the ambient atmosphere and equalizing the pressure within the expansion chamber to about ambient pressure level, augmenting the expansion chamber with at least one ejector, where each ejector functions as a dilutor and in-line pump pulling the exhaust sample at a constant pressure level from the center line of the expansion chamber at an effective distance downstream from the expansion chamber inlet and upstream from the open end of the expansion chamber and pushing diluted the samples downstream, and testing the diluted sample with at least one particle matter measurement instrument.

Another aspect of the invention relates to sampling apparatuses to testing particle emissions from aircraft engine(s) including, at least one inlet probe mounted on the aircraft engine ext plane with the probe inlet facing the exhaust plume perpendicular at the corner of the plume cross section, at least one expansion chamber associated with the probe, where the probe directs a flow of exhaust sample through the expansion chamber to ensure low particle matter resident time within the expansion chamber and prevent ambient air from entering the expansion chamber, the expansion chamber expands within the exhaust sample having an inlet which discharges any excess exhaust through an open end to the ambient atmosphere and equalizes the pressure within the expansion chamber to about ambient pressure level, the expansion chamber is associated with at least one ejector, where each ejector acts as a dilutor and in-line pump that pulls the exhaust sample at a constant pressure level from the center line of the expansion chamber at an effective distance downstream from the expansion chamber inlet and upstream from the open end of the expansion chamber and pushes and dilutes the sample downstream, and at least one particle matter instrument associated with the expansion chamber to test the diluted sample.

In embodiments, the probe inlet has a diameter of about ⅛ inch to about ½ inch with smaller inlet probe being used for higher thrust engines. In embodiments, the invention further includes placing the ejector inlet about 8 chamber diameters downstream within the expansion chamber and about 2 chamber diameters upstream from the open end of the expansion chamber. In other embodiments, the invention further includes placing the ejectors in series to create greater pumping effect and wider dilution range. In yet other embodiments, the invention further includes utilizing different sizes of ejectors to create greater pumping effect and wider dilution range.

In embodiments, the particle matter instrument is tailored to measure particle mass, number, and/or size distribution instruments. In other embodiments, the instruments are utilized for the detection of undiluted and diluted $CO_2$ concentrations to determine the dilution factor. In embodiments, the probe includes, but is not limited to, a button-hook construct for PM measurement for minimal particle loss.

The applicant in AESO developed a sampling system that is easy to set up and practical to use (requires two people to operate). The sampling system uses downstream dilution, functions smoothly with large pressure variations at the probe, is able to deliver samples through a long line (140 ft) at a pressure level of >13.4 PSI that is acceptable to PM measurement instruments. In addition, the sampling system allows one steady sample flow rate through the sampling line under different dilution ratios which simplifies PM line loss corrections.

The sampling system 10 includes three key components: a large inlet probe 14, an expansion chamber 20 with one end open to the ambient atmosphere, and an ejector dilutor 22 (see FIG. 1). The concepts of each individual component of this sampling system are not new. The large probe (button hook probe) has been used in the EPA Method 5 for PM sampling. The ejector has been used as a dilutor and an "in-line" pump in many previous applications. A cone-shaped sampling device for expanding the aircraft exhaust before sampling has also been applied. However, each of the above components functioning alone cannot overcome the challenges that aircraft PM emission measurement methods are faced with today. The combined use of the three components is the core of this innovation that allows the sampling system to work effectively under the challenging aircraft PM sampling conditions.

Sampling System Working Principal:

The large inlet probe directs a high sample flow through the expansion chamber to ensure low PM resident time within the expansion chamber and also prevents ambient air from entering the expansion chamber.

The expansion chamber expands the exhaust sample, discharging any excess amount of exhaust to the ambient atmosphere and equalizes the pressure within the expansion chamber to about ambient pressure level. The expansion chamber effectively shields the downstream dilution stage and PM measurement instruments from the large pressure variation at the probe tip. This construct allows the instruments downstream to function smoothly under stable pressure conditions during testing of any size engine at all power settings.

Figure 4:
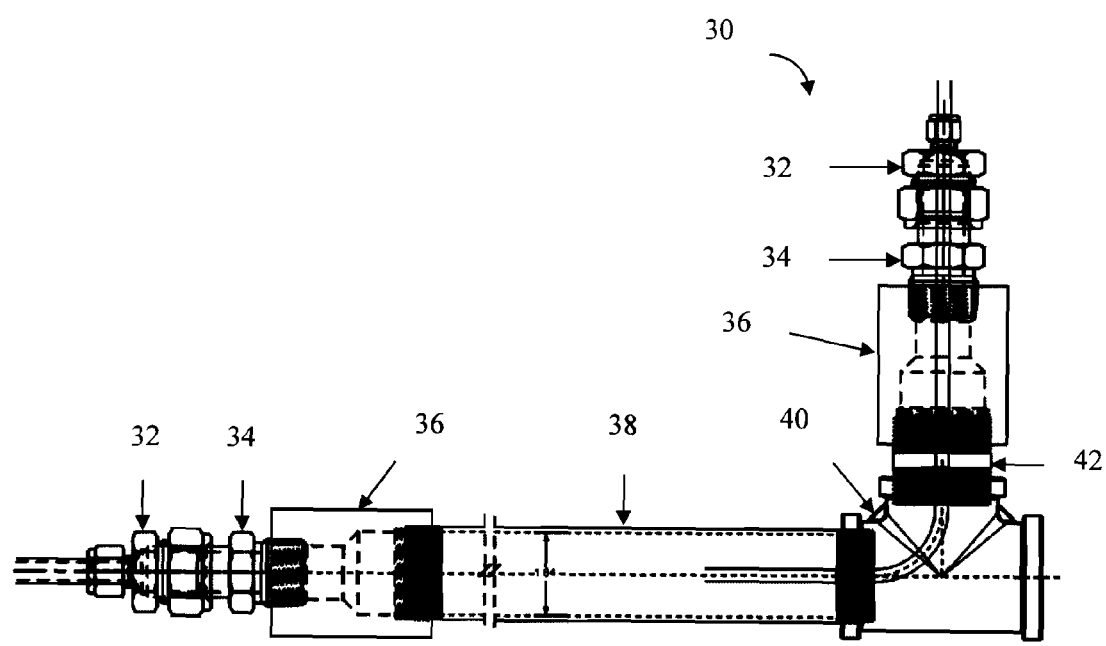
FIG. 4 is a side perspective view of an expansion chamber or tube, according to embodiments of the invention.

FIG. 4 illustrates an embodiment of an expansion chamber 30 or tube. The expansion chamber 30 has an inlet connected to the probe 14, an open end leading to the ambient atmosphere, and an inlet 18 leading to the ejector 22. An embodiment of the invention includes: 2 Swagelok tube fitting reducing unions 1 in×½ in 32 (Tube OD), 2 Swagelok tube fitting male tube adapters 34 1 in tube OD×1 in (male NPT), 2 stainless steel thread reducing couplings 36 (1½ in NPT 11½ treads per inch), a standard wall type threaded pipe 1½ in pipe, 1.900 inch OD, 18 mL, ²³⁄₃₂ in thread length 38, a stainless steel threaded tee 40, and a type 316/316L stainless steel pipe nipple 42 (Shown in FIGS. 1 and 4).

The ejector functions as a dilutor by adding particle-free air to the exhaust sample.

The ejector also acts as an "in-line" pump, pulling exhaust samples at approximately ambient pressure levels from the center of the expansion chamber, eight chamber diameters downstream from the expansion chamber inlet, at least two chamber diameters upstream from the outlet of the expansion chamber, and pushing the diluted sample 24 through the sample line to the instruments 26.

The total sample flow within the sample line downstream, F_total, is the sum of the sample flow demanded by the measurement instruments 26 plus any bypass flow construct to shorten the PM residence time within the sampling line. The F_total is a mixture of dilution air (F_air) and exhaust sample air. The dilution ratio, DR, can be expressed as DR= (F_total−F_air)/F_total. Accurate DR is determined by the ratios of measured undiluted $CO_2$ and diluted $CO_2$ concentrations. The compatibility of the dilution air flow demand, sample demand by the instrument, bypass flow rate and the ejector size need to be pre-tested. Under this dilution setting, the ejector (and the instrument downstream) only have to pull the needed amount of exhaust sample, largely determined by the difference between the F_total and the dilution air flow rate, leaving the total flow through the main sampling line unchanged under different dilution ratios. With a consistent sample flow rate, the PM line loss corrections can be greatly simplified.

With a stable pressure within the exhaust chamber and a fixed total sample flow within the main sample line downstream, the system dilution ratio can be controlled by adjusting the flow rate of dilution air through the ejector. More than one ejector can be used in series or a different size of ejector can be used to create a different dilution range when needed.

Experiment

The objective was to develop a simple but robust sampling and dilution system that can function smoothly under any engine exit plane pressure condition. The AESO's sampling method was tested extensively in the lab, as documented in the applicant's notebook, on flow rate and dilution ratios. For testing purposes, it was deployed side-by-side with the probe tip dilution method during an engine test.

Figure 2:
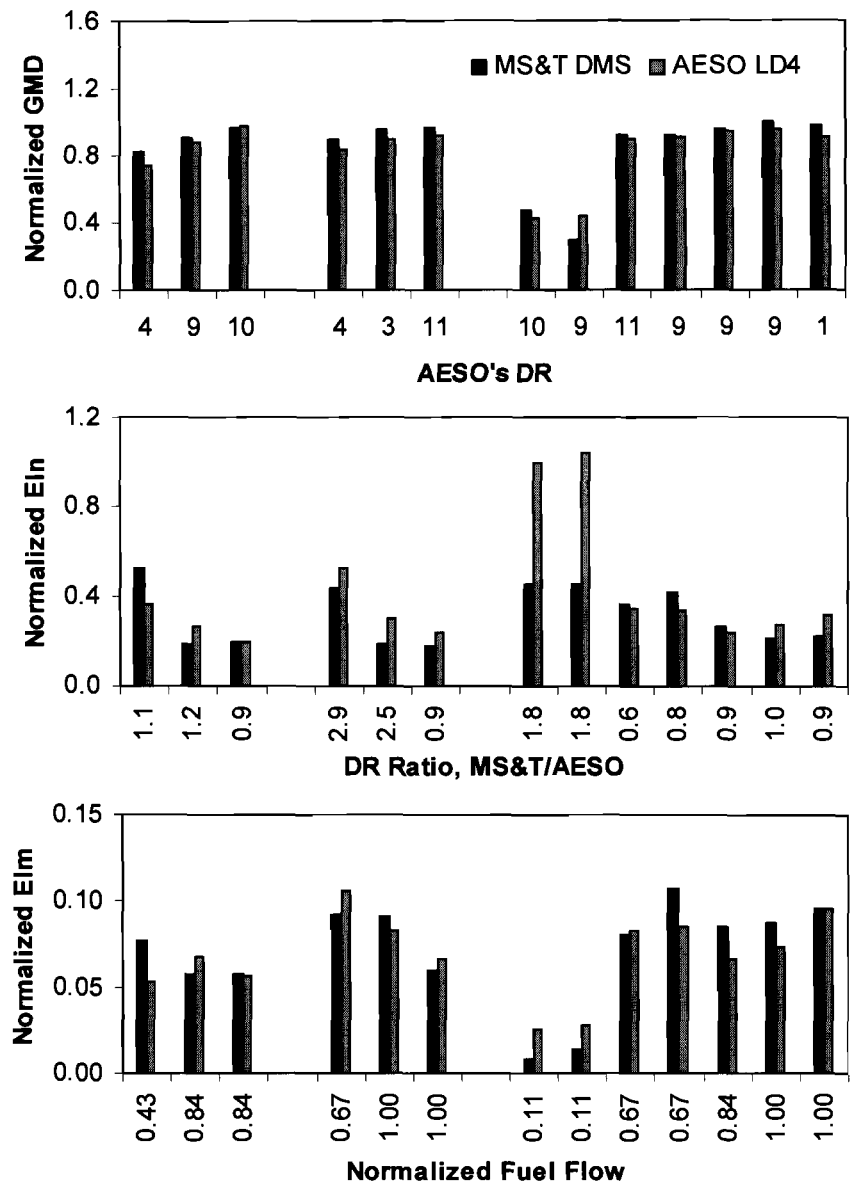
FIG. 2 is a set of graphs which show the data measured simultaneously by a downstream dilution method (AESO) and the probe tip dilution method (Missouri University Science and Technology, MS&T). Particle properties, geometric mean diameter (GMD) of particle size distribution, normalized particle number emission index (EIn) and mass emission index (EIm) are shown, according to embodiments of the invention.
Figure 3:
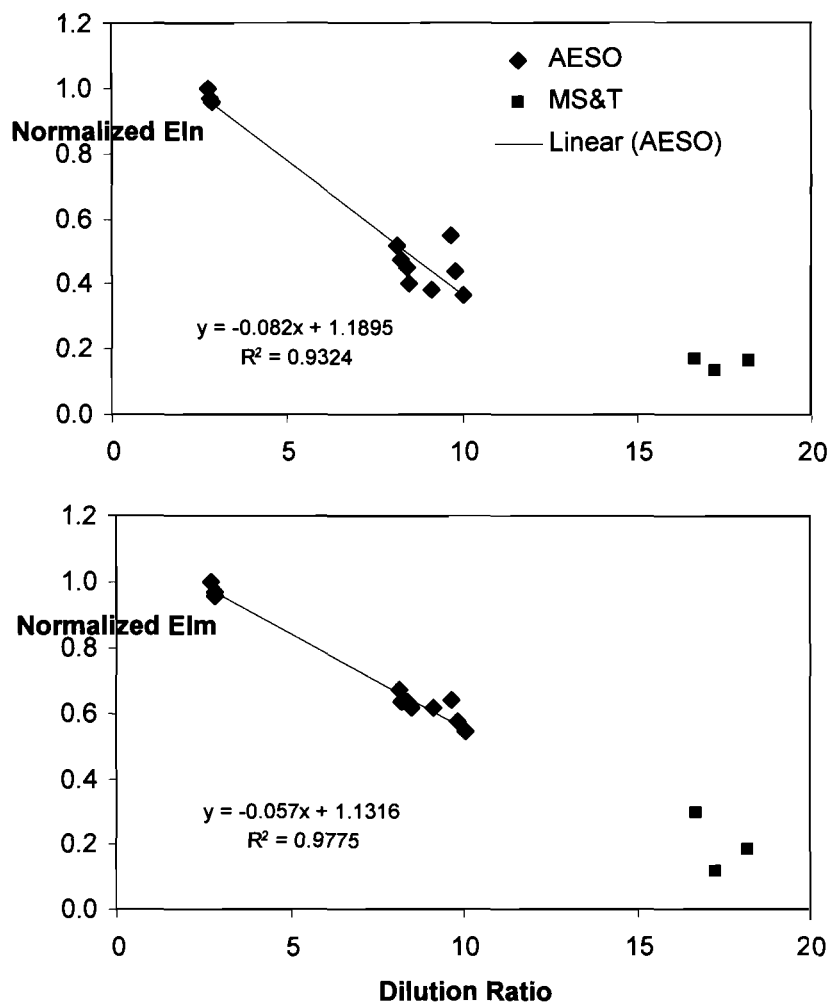
FIG. 3 is a set of graphs which show the normalized particle number emission index (EIn) and mass emission index (EIm) as compared to exhaust sample dilution ratios measured under an idle power condition, according to embodiments of the invention.

AESO's PM sampling system validation FIG. 2 shows the data measured simultaneously by AESO's downstream dilution method and the more accepted probe tip dilution method (used by MS&T) including the geometric mean diameter (GMD) of particle size distribution, normalized particle number emission index (EIn) and mass emission index (EIm). The large disagreements at lower power settings are mainly caused by the different dilution ratio used by the two methods. FIG. 3 shows the correlation between the dilution ratio and the measured EIn and EIm by the two methods under idle power conditions. From the linear pattern, it is reasonable to predict a good agreement between the two methods even for low power settings should similar dilution ratios be used by both methods.

The agreement between data measured simultaneously using AESO's downstream (12 feet) dilution method and that using the probe tip dilution method is on the same order as that for repeated measurements by either method, suggesting that downstream (12 feet) dilution did not cause any significant differences in PM properties.

Major advantages of the invention include, but are not limited to, aircraft emissions measurements. Performance testing and the comparison results showed that the simple sampling system AESO developed successfully resolved aircraft PM sampling challenges: diluting exhaust samples 12 feet 16 downstream and yielding similar data as probe tip dilution; functioning smoothly at any engine power setting with any exhaust pressure variations; delivering exhaust samples through a 140 feet sample line at pressure >13.4±0.08 PSI; and delivering samples under a stable sample flow rate under different dilution ratios. This sampling system will greatly lower the aircraft PM emission test costs by reducing man power requirements and engine run time per/PM emission test.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A sampling method for testing particle emissions from aircraft engine(s), comprising:
    mounting one inlet probe at said aircraft engine exit plane with said probe inlet facing the exhaust plume substantially perpendicularly at the center of said plume cross section;
    associating one expansion chamber with said probe, wherein said probe is directing a flow of exhaust sample through said expansion chamber ensuring low particle matter resident time within said expansion chamber and allowing substantially no ambient air to enter said expansion chamber;
    expanding said exhaust sample within said expansion chamber having an expansion chamber inlet, discharging any excess exhaust through an open end to the ambient atmosphere and equalizing the pressure within said expansion chamber to about ambient pressure level;
    connecting said expansion chamber with at least one ejector having an ejector inlet, wherein each said ejector functions as a dilutor and in-line pump pulling said exhaust sample at a constant pressure level from the center line of said expansion chamber at an effective distance downstream from said expansion chamber inlet and upstream from said open end of said expansion chamber and pushing diluted said samples downstream; and
    testing said diluted sample with at least one particle matter measurement instrument.

2. The method according to claim 1, wherein said probe inlet having a diameter of about ⅛ inch to about ½ inch, with smaller said inlet probe being used for higher thrust engines.

3. The method according to claim 1, further comprising placing said ejector inlet about 8 chamber diameters downstream from said expansion chamber inlet and about 2 chamber diameters upstream from said open end of said expansion chamber.

4. The method according to claim 1, further comprising placing said ejectors in series to create greater pumping effect and wider dilution range.

5. The method according to claim 1, further comprising utilizing different sizes of ejectors to create greater pumping effect and wider dilution range.

6. The method according to claim 1, wherein said particle matter instrument measures at least one of particle mass, particle number, and/or particle size distribution instruments.

7. The method according to claim 1, wherein said instruments utilize detection of undiluted and diluted $CO_2$ concentrations to determine dilution factor.

8. The method according to claim 1, wherein said probe comprises a button-hook construct.

9. The method according to claim 1, wherein said ejector pulls said exhaust sample at about 1 atm, at ambient condition, to stabilize said ejector's functionality.

10. The method according to claim 1, wherein said ejector pushes said diluted sample to particle matter measurement instruments at pressures greater than about 13.4±0.08 PSI.

11. A sampling apparatus to testing particle emissions from aircraft engine(s), comprising:
    at least one inlet probe mounted on said aircraft engine exit plane with said probe inlet facing the exhaust plume;
    at least one expansion chamber associated with said probe, wherein said probe directs a flow of exhaust sample through said expansion chamber to ensure low particle matter resident time within said expansion chamber and prevent ambient air from entering said expansion chamber;
    said exhaust sample expands within said expansion chamber having an inlet which discharges any excess exhaust through an open end to the ambient atmosphere and equalizes the pressure within said expansion chamber to about ambient pressure level;
    said expansion chamber is associated with at least one ejector, wherein each said ejector acts as a dilutor and in-line pump that pulls said exhaust sample at a constant pressure level from the center line of said expansion chamber at an effective distance downstream from said expansion chamber inlet and upstream from said open end of said expansion chamber and pushes and dilutes said sample downstream; and
    at least one particle matter instrument associated with said expansion chamber to test said diluted sample.

12. The apparatus according to claim 11, wherein said probe inlet having a diameter of about ⅛ inch to about ½ inch.

13. The apparatus according to claim 11, further comprising said ejector inlet being about 8 chamber diameters downstream within said expansion chamber and about 2 chamber diameters upstream from said open end of said expansion chamber.

14. The apparatus according to claim 11, further comprising said ejectors in series to create greater pumping effect and wider dilution range.

15. The apparatus according to claim 11, further comprising different sizes of ejectors to create greater pumping effect and wider dilution range.

16. The apparatus according to claim 11, wherein said particle matter instrument measures at least one of particle mass, particle number, and/or particle size distribution instruments.

17. The apparatus according to claim 11, wherein said instruments utilize detection of undiluted and diluted $CO_2$ concentrations to determine dilution factor.

18. The apparatus according to claim 11, wherein said probe comprises a button-hook construct.

19. The apparatus according to claim 11, wherein said ejector pulls said exhaust sample at about 1 atm, at ambient condition, to stabilize said ejector's functionality.

20. The apparatus according to claim 11, wherein said ejector pushes said diluted sample to at least one said particle matter instrument at about pressures greater than 13.4 PSI.

* * * * *